US009023036B2

(12) United States Patent
Govari et al.

(10) Patent No.: US 9,023,036 B2
(45) Date of Patent: May 5, 2015

(54) LASSO CATHETER WITH TIP ELECTRODE

(71) Applicant: Biosense Webster (Israel), Ltd., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 222 days.

(21) Appl. No.: 13/707,974

(22) Filed: Dec. 7, 2012

(65) Prior Publication Data

US 2014/0163546 A1 Jun. 12, 2014

(51) Int. Cl.
*A61B 18/18* (2006.01)
*A61B 18/14* (2006.01)
*A61B 18/12* (2006.01)

(52) U.S. Cl.
CPC ......... *A61B 18/1492* (2013.01); *A61B 18/1206* (2013.01)

(58) Field of Classification Search
USPC .......................................... 606/41
See application file for complete search history.

(56) References Cited

U.S. PATENT DOCUMENTS

| 7,108,696 B2 * | 9/2006 | Daniel et al. ............ 606/41 |
| 2005/0033135 A1 | 2/2005 | Govari |
| 2010/0168548 A1 | 7/2010 | Govari et al. |
| 2011/0160719 A1 | 6/2011 | Govari et al. |

FOREIGN PATENT DOCUMENTS

WO   WO 96/05768 A1   2/1996

* cited by examiner

*Primary Examiner* — George Manuel
(74) *Attorney, Agent, or Firm* — Wayne C. Jaeschke, Jr.

(57) ABSTRACT

Medical apparatus includes a sheath having a lumen with a distal opening. A flexible probe, which is adapted for insertion through the sheath, includes an insertion shaft, an end section, which is connected to the distal end of the insertion shaft, a tip electrode extending over the tip of the end section, and proximal electrodes distributed along the end section. The probe is manipulable, within the sheath, between a retracted configuration in which the end section is contained within the lumen so that only the tip electrode protrudes through the distal opening, and an extended configuration in which the entire end section protrudes from the distal opening and assumes an arcuate shape. An energy generator applies electrical energy only to the tip electrode while the probe is in the retracted configuration and to at least the proximal electrodes while the probe is in the extended configuration.

6 Claims, 4 Drawing Sheets

LASSO CATHETER WITH TIP ELECTRODE

FIELD OF THE INVENTION

The present invention relates generally to methods and devices for invasive medical treatment, and specifically to catheters.

BACKGROUND OF THE INVENTION

Ablation of myocardial tissue is well known as a treatment for cardiac arrhythmias. In radio-frequency (RF) ablation, for example, a catheter is inserted into the heart and brought into contact with tissue at a target location. RF energy is then applied through an electrode on the catheter in order to create a lesion for the purpose of breaking arrhythmogenic current paths in the tissue.

Recently, circumferential ablation of the ostia of the pulmonary veins has gained acceptance as a treatment for atrial arrhythmias, and particularly for atrial fibrillation. For example, U.S. Pat. No. 6,064,902 describes a catheter for ablating tissue on the inner wall of a blood vessel, such as a pulmonary vein. The tip portion of the catheter is deflectable from a first, generally straight, configuration, in which the proximal and distal sections are substantially co-linear, to a second, J-shaped, configuration in which the proximal and distal sections are generally parallel with a separation therebetween substantially corresponding to the inside diameter of the blood vessel. The distal end portion of the catheter is rotated about the longitudinal axis of the catheter to cause a circumferential displacement of proximal and distal ablation electrodes on the catheter along the inner wall of the pulmonary vein. In this way, the electrode catheter may be used to ablate a number of circumferentially-spaced sites on the inner wall of the pulmonary vein by ablating one or two sites at each circumferential position.

U.S. Patent Application Publication 2005/0033135, whose disclosure is incorporated herein by reference, describes a lasso for pulmonary vein mapping and ablation. A catheter for circumferentially mapping a pulmonary vein (PV) includes a curved section shaped to generally conform to the shape of the interior surface of the PV. The curved section comprises one or more sensing electrodes, and its proximal end is joined at a fixed or generally known angle to a base section of the catheter. Position sensors are fixed to the curved section of the catheter and to the distal end of the base section. The catheter is inserted into the heart, and the curved section is positioned in contact with the wall of the PV, while the base section remains within the left atrium, typically positioned such that the joint with the curved section is at the ostium of the vein. The information generated by the three position sensors is used to calculate the locations and orientations of the sensing electrodes, which enables mapping of the surface of the PV. The sensing electrodes may additionally perform ablation of selected sites, or the catheter may further comprise ablation elements.

U.S. Patent Application Publication 2010/0168548, whose disclosure is incorporated herein by reference, describes a lasso catheter for use in a system for electrical mapping of the heart. The catheter has an array of raised, perforated electrodes, which are in fluid communication with an irrigating lumen. There are position sensors on a distal loop section and on a proximal base section of the catheter. The electrodes are sensing electrodes that may be adapted for pacing or ablation. The raised electrodes securely contact cardiac tissue, forming electrical connections having little resistance.

U.S. Patent Application Publication 2011/0160719, whose disclosure is incorporated herein by reference, describes a catheter with an arcuate end section. The end section is formed so as to define, when unconstrained, an arc oriented obliquely relative to the axis of the catheter shaft and having a center of curvature on the axis. One or more electrodes are disposed at respective locations along the end section. In some embodiments, these electrodes include a tip electrode extending over the tip and a plurality of proximal electrodes distributed along the end section. The end section is configured so that when the unconstrained end section is advanced axially against a tissue surface in the body, the end section engages the tissue surface along the arc so that the tip electrode and at least some of the proximal electrodes contact the tissue surface simultaneously. Optionally, the end section includes one or more joints, which can be straightened and steered so as to bring the tip electrode alone into contact with the tissue surface.

SUMMARY

Embodiments of the present invention that are described hereinbelow provide invasive devices and methods for contacting tissue within the body with enhanced ease and versatility.

There is therefore provided, in accordance with an embodiment of the present invention, medical apparatus, which includes a sheath, adapted for insertion into a body of a patient and having a lumen with a distal opening. A flexible probe is adapted for insertion through the sheath and includes an insertion shaft, having a distal end; an end section, which is connected to the distal end of the insertion shaft and includes a distal tip; a tip electrode extending over the tip; and a plurality of proximal electrodes distributed along the end section. The probe is manipulable, within the sheath, between a retracted configuration in which the end section is contained within the lumen so that only the tip electrode protrudes through the distal opening, and an extended configuration in which the entire end section protrudes from the distal opening and assumes an arcuate shape. An energy generator is configured to apply electrical energy only to the tip electrode while the probe is in the retracted configuration and to apply the electrical energy to at least the proximal electrodes while the probe is in the extended configuration.

In disclosed embodiments, the end section is resilient and is formed so as to define, when unconstrained, the arcuate shape. Typically, the end section is configured so that when the unconstrained end section is advanced axially against a tissue surface in the body, the end section engages the tissue surface along the arc so that the tip electrode and at least some of the proximal electrodes contact the tissue surface simultaneously.

In some embodiments, the probe includes a transducer, which is configured to provide a signal indicating that the probe is in the retracted configuration. The transducer may be one of multiple position transducers, which are disposed along the end section and are configured to provide signals indication of a position of the end section within the body. Additionally or alternatively, the sheath includes a positioning element in proximity to the distal opening, wherein the energy generator is configured to apply the electrical energy only to the tip electrode when the signal provided by the transducer indicates that the transducer is within a predetermined minimum distance of the positioning element.

In a disclosed embodiment, the sheath and the probe are adapted for insertion into a chamber of a heart within the body, so as to bring the tip electrode and proximal electrodes into contact with myocardial tissue in the chamber, and application of the electrical energy through the electrodes ablates the myocardial tissue with which the electrodes are in contact.

There is also provided, in accordance with an embodiment of the present invention, a method for treatment, which includes inserting a sheath, having a lumen with a distal opening, into body of a patient. A flexible probe is inserted through the sheath so that an end section, at a distal end of the probe, protrudes from the distal opening and assumes an arcuate shape. While the end section protrudes from the distal opening, the arcuate shape is brought into contact with tissue in the body, and a plurality of electrodes, distributed along the end section, are actuated to apply electrical energy to the tissue. The flexible probe may also be withdrawn into the sheath so that the end section is contained within the lumen and only a tip electrode, at a distal tip of the end section, protrudes through the distal opening. While the end section is contained within the lumen, the tip electrode is brought into contact with the tissue, and only the tip electrode is actuated with the electrical energy.

There is additionally provided, in accordance with an embodiment of the present invention, a medical probe, which includes a flexible insertion shaft, having a distal end and an end section, which is connected to the distal end of the insertion shaft and comprises a distal tip. A perforated tip electrode extends over the tip, and a plurality of perforated proximal electrodes are distributed along the end section. A first irrigation lumen within the insertion shaft is coupled to convey an irrigation fluid to the tip electrode, while a second irrigation lumen within the insertion shaft, separate from the first irrigation lumen, is coupled to convey the irrigation fluid to the proximal electrodes.

The present invention will be more fully understood from the following detailed description of the embodiments thereof, taken together with the drawings in which:

DETAILED DESCRIPTION OF EMBODIMENTS

Embodiments of the present invention that are described hereinbelow provide a flexible invasive probe, such as a catheter, with an arcuate end section and a sheath, which be used simply and conveniently to make contact with the surface of an organ either along an arc or at individual points. The operator chooses between the arcuate configuration and of the end section and a straight configuration, for contacting individual points, by advancing and retracting the probe through the sheath.

In the disclosed embodiments, the end section comprises a tip electrode and multiple proximal electrodes distributed along the length of the end section, which can be actuated to ablate tissue with which the electrodes are in contact. In the straight configuration, only the tip electrode is actuated, whereas in the arcuate configuration, all of the electrodes may be actuated to create arcuate lesions in the tissue. The disclosed combination of the catheter with the sheath thus provides a simple, practical way in which a lasso catheter can be used for single-point ablation, without requiring substantial mechanical modification to existing lasso catheter designs. The added point-ablation capability of the lasso catheter obviates the need to remove the lasso catheter and insert a different, straight catheter when point ablation is needed.

Figure 1:
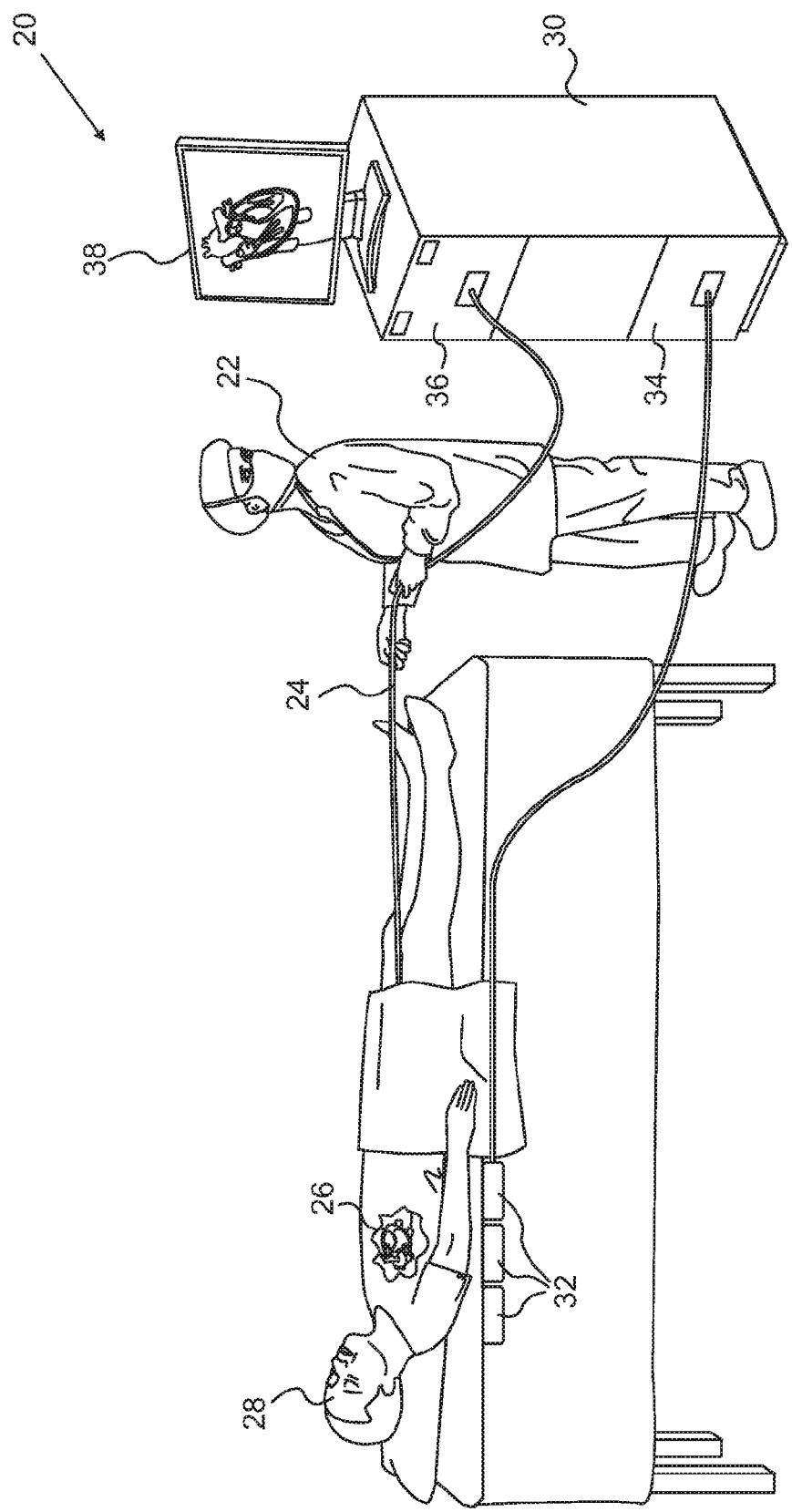
FIG. 1 is a schematic pictorial illustration of a system for ablation of tissue in the heart, in accordance with an embodiment of the present invention.

FIG. 1 is a schematic pictorial illustration of a system 20 for ablation of tissue in a heart 26 of a patient 28, in accordance with an embodiment of the present invention. An operator 22, such as a cardiologist, inserts a flexible probe, such as a catheter 24, through the vascular system of patient 28 so that the distal end of the catheter enters a chamber of the patient's heart. Operator 22 advances the catheter so that the end section of the catheter engages endocardial tissue at a desired location or locations, as shown in the figures that follow. Catheter 24 is connected by a suitable connector (not shown) at its proximal end to a console 30. The console comprises an RF generator 36 for applying RF energy through electrodes on the end section of the catheter in order to ablate the tissue contacted by the distal section. Alternatively or additionally, catheter 24 may be used for other diagnostic and/or therapeutic functions, such as intracardiac electrical mapping or other types of ablation therapy, including diagnostic and therapeutic functions in organs other than the heart.

Figure 3:
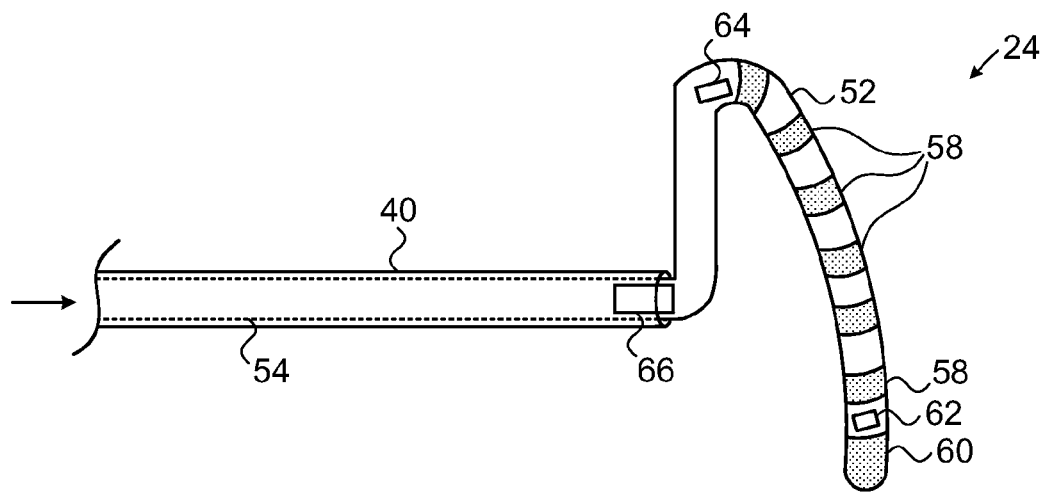
FIG. 3 is a schematic side view of a catheter in a curved configuration, in accordance with an embodiment of the present invention.
Figure 4:
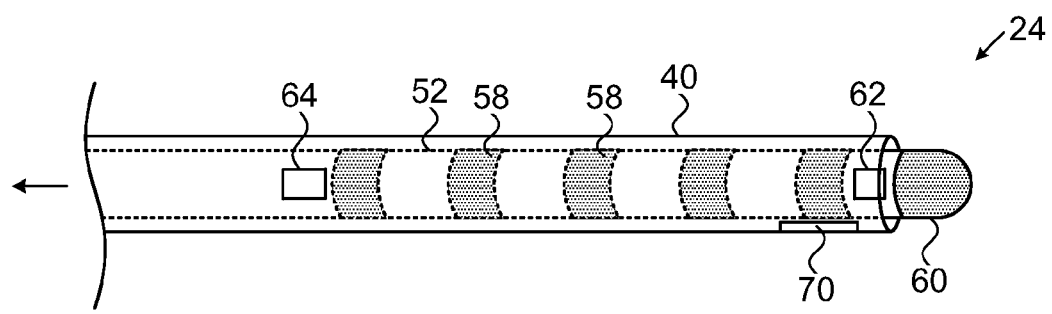
FIG. 4 is a schematic side view of the catheter of FIG. 3 in a straight configuration, in accordance with another embodiment of the present invention.

In the pictured embodiment, system 20 uses magnetic position sensing to determine position coordinates of the end section of the catheter inside heart 26. To determine the position coordinates, a driver circuit 34 in console 30 drives field generators 32 to generate magnetic fields within the body of patient 28. Typically, field generators 32 comprise coils, which are placed below the patient's torso at known positions external to the body. These coils generate magnetic fields in a predefined working volume that contains heart 26. One or more magnetic field sensors within the end section of catheter 24 (as shown in FIGS. 3 and 4) generate electrical signals in response to these magnetic fields. The console processes these signals in order to determine the position (location and/or orientation) coordinates of the end section of catheter 24, and possibly also the deformation of the end section, as explained below. Console 30 may use the coordinates in driving a display 38 to show the location and status of the catheter. This method of position sensing and processing is described in detail, for example, in PCT International Publication WO 96/05768, whose disclosure is incorporated herein by reference, and is implemented in the CARTO™ system produced by Biosense Webster Inc. (Diamond Bar, Calif.).

Alternatively or additionally, system 20 may comprise an automated mechanism (not shown) for maneuvering and operating catheter 24 within the body of patient 28. Such mechanisms are typically capable of controlling both the longitudinal motion (advance/retract) and the rotation of catheter 24. In such embodiments, console 30 generates a control input for controlling the motion of the catheter based on the signals provided by the position sensing system.

Although FIG. 1 shows a particular system configuration, other system configurations may be used in alternative embodiments of the present invention. For example, the methods described hereinbelow may be applied using position transducers of other types, such as impedance-based or ultrasonic position sensors. The term "position transducer" as used herein refers to an element mounted on or in catheter 24 that causes console 30 to receive signals indicative of the coordinates of the element. The position transducer may thus comprise a receiver in the catheter, which generates a position signal to the control unit based on energy received by the transducer; or it may comprise a transmitter, emitting energy that is sensed by a receiver external to the probe. Furthermore, the methods described hereinbelow may similarly be applied in mapping and measurement applications using not only catheters, but also probes of other types, both in the heart and in other body organs and regions.

Figure 2:
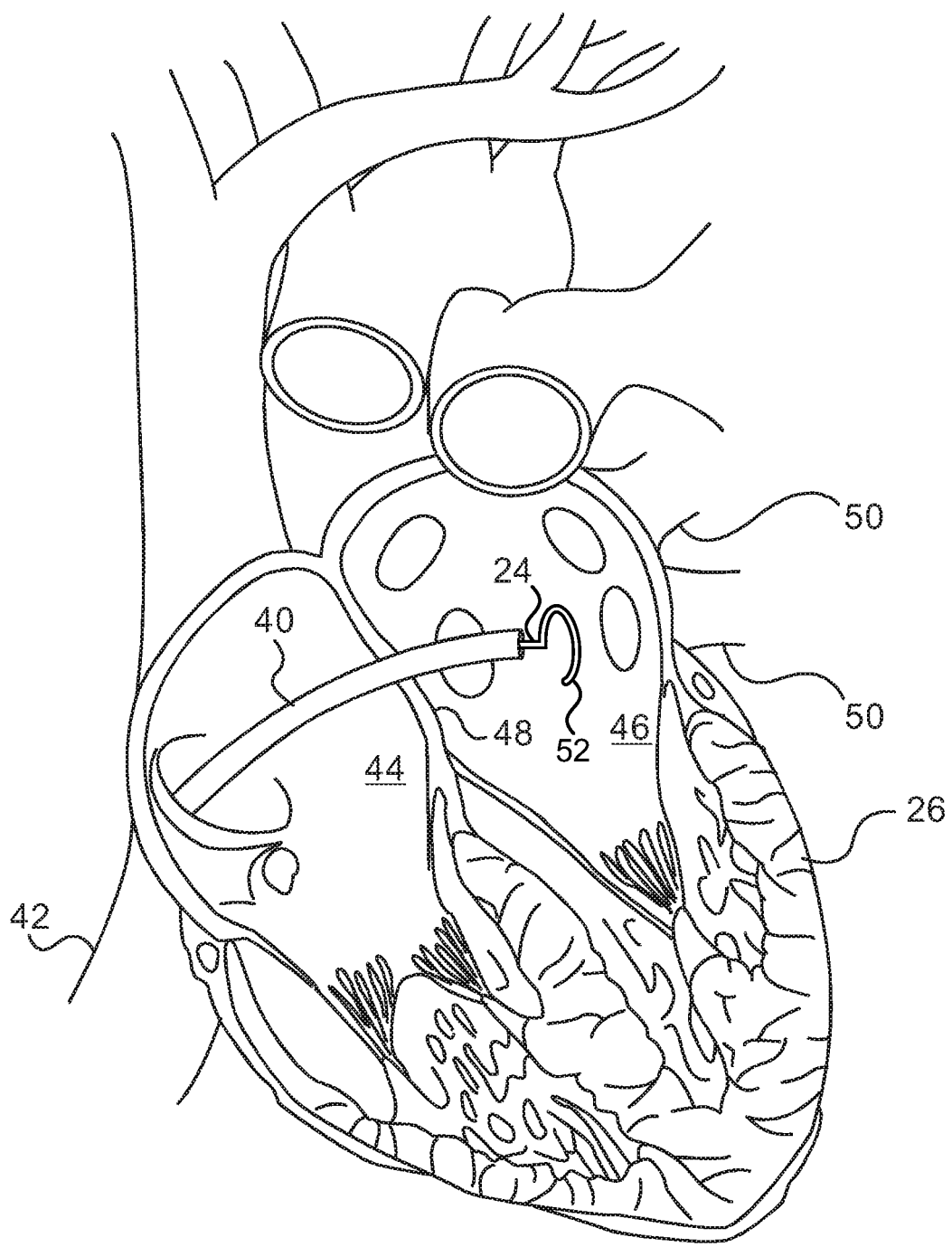
FIG. 2 is a schematic sectional view of a heart showing insertion of a catheter into the left atrium, in accordance with an embodiment of the present invention.

FIG. 2 is a schematic sectional view of heart 26, showing insertion of catheter 24 into the heart, in accordance with an embodiment of the present invention. To insert the catheter in the pictured embodiment, the operator first passes a sheath 40 percutaneously through the vascular system and into right atrium 44 of the heart through ascending vena cava 42. The sheath penetrates through interatrial septum 48, typically via the fossa ovalis, into left atrium 46. Alternatively, other approach paths may be used. Catheter 24 is then inserted through the lumen of sheath 40 until an end section 52 of the catheter passes out of the distal opening at the end of the sheath into the left atrium, as shown in the figure. The end section is formed so as to define an arc when unconstrained, as is shown and described in greater detail hereinbelow with reference to FIG. 3. While end section 52 is passing through sheath 40, however, the smaller inner diameter of the sheath holds the end section straight and roughly parallel to the catheter axis, as shown in FIG. 4.

Operator 22 aligns the longitudinal axis of sheath 40 (and of catheter 24) inside left atrium 46 with the axis of one of pulmonary veins 50. The operator may carry out this alignment using the position sensing methods described above, along with a pre-acquired map or image of heart 26. Alternatively or additionally, the alignment may be performed under fluoroscopic or other means of visualization. The operator advances end section 52 of the catheter toward the target pulmonary vein so that the arc contacts the ostium, and the end section either partly or fully surrounds the vein (depending on the angle subtended by the arc). The operator then rotates the catheter about its axis within the sheath so that the end section traces an annular path around the circumference of the vein. Meanwhile, the operator actuates RF generator 36 to ablate the tissue along the path. After completing this procedure around one pulmonary vein, the operator may shift the sheath and catheter and repeat the procedure around one or more of the other pulmonary veins.

After performing ablation along such an annular path, operator 22 may assess the extent and quality of the ablation by various means that are known in the art, such as ultrasonic sensing, magnetic resonance imaging (MRI), or measurement of local electrical properties of the tissue (such as impedance and/or activation voltage). If the operator discovers by such means (or in any other manner) that a certain point or points have not been sufficiently ablated, the operator may withdraw catheter into sheath 40 until only the distal tip of end section 52 protrudes from the sheath. This sort of configuration is shown in FIG. 4 and is described in greater detail with reference thereto. In this latter configuration, the operator may advance the sheath and catheter so that only the distal tip of the catheter contacts the tissue at each point requiring further ablation. While the catheter contacts the tissue in this manner, the tip electrode of the catheter may be energized by RF generator 36 to ablate the tissue.

FIG. 3 is a schematic side view of the distal portion of catheter 24, including end section 52 in its extended, arcuate configuration, in accordance with an embodiment of the present invention. The catheter comprises an insertion shaft 54, which connects at its distal end to the base of end section 52. Shaft 54 and end section 52 typically comprise an outer shell made from a suitable flexible biocompatible material, such as polyurethane, having a diameter around 2-3 mm, with internal wires and tubing as required. In one embodiment, in which the catheter is designed for therapeutic ablation, the size of the shaft is 7 Fr (about 2.3 mm diameter), while the end section is of the same or slightly larger size (such as 7.5 Fr). In other embodiments, for diagnostic measurements, the shaft is 7 Fr, while the end section has a diameter between 1 and 2.5 mm.

End section 52 is formed as a complete or partial lasso, i.e., as a preformed arcuate structure, which typically subtends between 180° and 360°. The radius of curvature of end section 52, when unconstrained, is typically between 7.5 mm and 15 mm. Because the arc structure is resilient and, possibly, slightly helical, when end section 52 is positioned in the heart (against the ostium of a pulmonary vein, for example), and insertion shaft 54 is advanced distally, the end section will press against the heart tissue over the entire length of the arc, thus facilitating good tissue contact. The arcuate and possibly helical shape of end section 52 may be maintained, for example, by incorporating a thin strut made from a shape memory material, such as Nitinol (not shown in the figures), in the desired shape within the end section. The strut is made sufficiently flexible to permit the end section to straighten during insertion and withdrawal through sheath 40, but to resume its arcuate form when it is unconstrained inside the heart chamber.

End section 52 comprises an array of electrodes along its length, including, in this example, a tip electrode 60 extending over the distal tip of the end section and proximal electrodes 58 distributed along the end section. Typically, electrodes 58 have a width between 1 mm and 4 mm, and are spaced between 1 mm and 10 mm apart. Electrodes 58 and 60 are connected to the connector at the proximal end of catheter 24 by wires (not shown) running through the catheter. Alternatively, other electrode configurations may be used. For example, the end section may include smaller "bump" electrodes, as described in the above-mentioned U.S. Patent Application Publication 2010/0168548. In any of these configurations, the electrodes may be used for sensing and/or ablation. In order to ablate an entire annulus around a pulmonary vein, for example, catheter 24 may be rotated ("clocked") about its axis while applying RF electrical energy to the electrodes, as noted above.

To provide local cooling and prevent adhesion during ablation, electrodes 58 and 60 may have perforations for irrigation. (Perforations of this type are described and shown, for example, in U.S. Patent Application Publication 2010/0168548.) The perforations are coupled to one or more lumens in end section 52, which carries irrigation fluid from shaft 54 to the electrodes and to the tissue surrounding them. Details of an arrangement of electrodes and irrigation lumens that may be used for this purpose are described hereinbelow with reference to FIG. 5.

Catheter 24 may also include one or more position transducers, such as positions sensors 62, 64 and 66. In this embodiment, sensors 62, 64 and 66 comprise coils, which output position signals in response to the magnetic fields of field generators 32 (FIG. 1). For example, sensor 66 may comprise three coils, which give full location and orientation information with regard to the base of end section 52, while sensors 62 and 64 each comprise a single coil, giving location and partial orientation information. This sort of arrangement is described further in the above-mentioned U.S. Patent Application Publication 2005/0033135. It enables console 30 to track both the base location and the deformation of end section 52, so that the operator can verify that the end section is properly located and in good contact with the tissue. Alternatively, other types of position transducers and sensing configurations may be used in catheter 24 and system 20. Sheath 40 may also comprise one or more position transducers, as shown in FIG. 4.

FIG. 4 is a schematic side view of the distal end of catheter 24, showing end section 52 in its retracted, straightened configuration, in accordance with an embodiment of the present invention. Catheter 24 has been withdrawn into sheath 40 so that only tip electrode 60 protrudes distally, while proximal electrodes 58 are held inside the sheath. With the catheter in this configuration, operator 22 may advance sheath 40 and catheter 24 together so that electrode 60 contacts particular points on the endocardium for purposes of electrical measurement and/or ablation. To ablate tissue in this configuration, RF generator 36 applies energy only to tip electrode 60, and proximal electrodes 58 are not actuated.

Optionally, sheath 40 may contain one or more position transducers 70, as well. The position signals provided by transducer 70 in proximity to the distal opening of sheath 40, for example, can be used for either or both of two purposes:

To detect the location of the sheath within the body relative to field generators 32, in order to assist operator 22 in navigating the sheath to the desired location; and To sense the disposition of end section 52 within the sheath.

A processor in console 30 may thus determine that catheter 24 is properly deployed in the straightened configuration of FIG. 4 when the position signals from transducers 62 and 70 indicate that they are located within a predetermined minimum distance of one another. Alternatively or additionally, the distance between transducers 62 and 70 may be determined by transmitting a signal from one of these transducers and receiving the signal at the other. RF generator 36 may be controlled automatically so that only tip electrode 60 can be energized as long as the remainder of end section 52 is contained in sheath 40.

Alternatively or additionally, other positioning elements may be used to sense the location of the distal tip of catheter 24 relative to sheath 40. For example, a magnetic structure at the end of the sheath may be used for this purpose, as described in U.S. patent application Ser. No. 13/467,158, whose disclosure is incorporated herein by reference. Similarly, other sorts of transducers in the probe and/or sheath, such as proximity sensors, may be used to ascertain the configuration of end section 52 relative to sheath 40.

Figure 5:
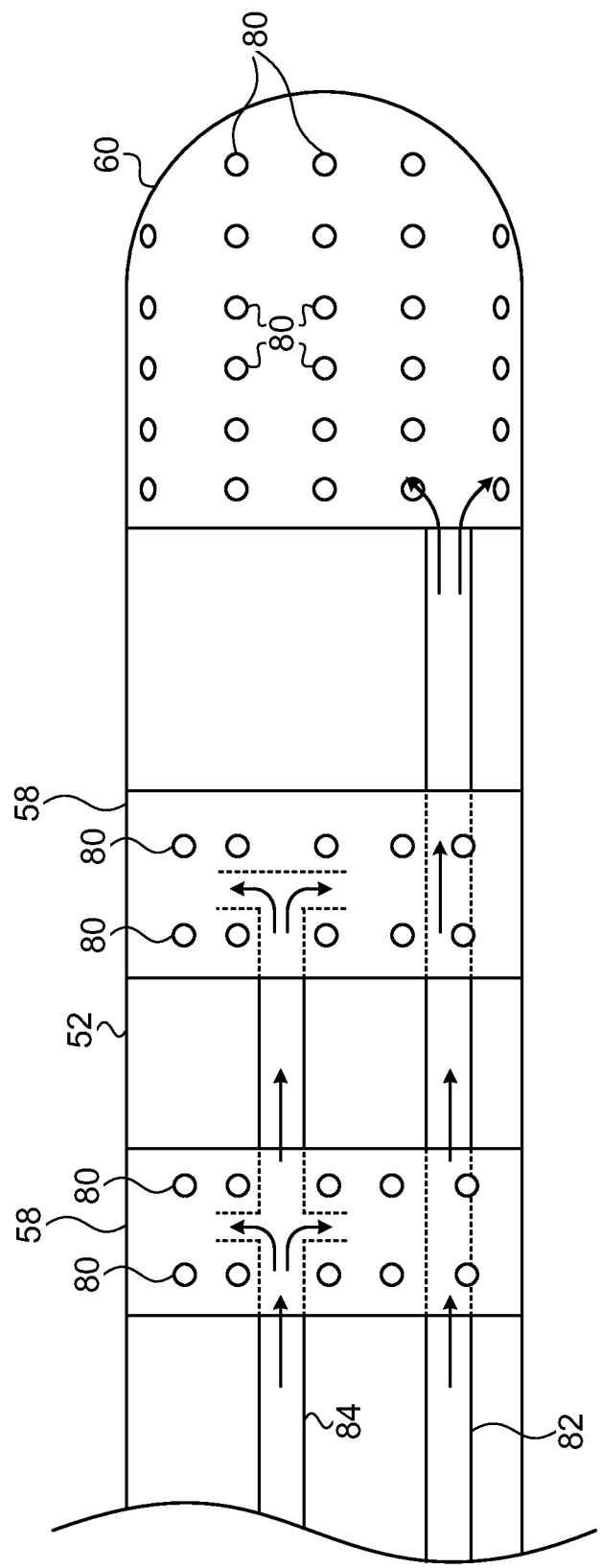
FIG. 5 is a schematic side view of the distal end of a catheter, in accordance with an embodiment of the present invention.

FIG. 5 is a schematic side view of the distal tip of end section 52 of catheter 24, in accordance with an embodiment of the present invention. In this embodiment, electrodes 58 and 60 have multiple perforations through which irrigation fluid may be delivered to tissue with which the catheter is in contact during ablation. Because tip electrode 60 may be actuated individually (in the configuration shown in FIG. 4, for example), separately from ring electrodes 58, it is desirable that the tip electrode be irrigated separately from the ring electrodes.

Thus, as shown in FIG. 5, tip electrode 60 is served by a separate irrigation lumen 82, while ring electrodes 58 are served by a common irrigation lumen 84. In the configuration shown in FIG. 3, in which both the tip and ring electrodes are actuated to ablate tissue, console 30 supplies irrigation fluid to catheter 24 via both of lumens 82 and 84, so that all electrodes are irrigated. On the other hand, in the configuration of FIG. 4, the console supplies irrigation fluid only to lumen 82. This sort of differential irrigation scheme may be applied, as well, to electrodes of other types (such as the bump electrodes shown in the above-mentioned U.S. Patent Application Publication 2010/0168548), and in substantially any other type of irrigated ablation probe in which multiple electrodes are actuated selectively.

Although the embodiments described above relate specifically to catheters for use in certain intracardiac procedures, probes made in accordance with the principles set forth in this patent application may similarly be used in diagnostic and therapeutic procedures of other types, both in the heart and in other body organs. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. Medical apparatus, comprising:
   a sheath, adapted for insertion into a body of a patient and having a lumen with a distal opening;
   a flexible probe, which is adapted for insertion through the sheath and comprises:
   an insertion shaft, having a distal end;
   an end section, which is connected to the distal end of the insertion shaft and comprises a distal tip;
   a tip electrode extending over the tip; and
   a plurality of proximal electrodes distributed along the end section,
   wherein the probe is manipulable, within the sheath, between a retracted configuration in which the end section is contained within the lumen so that only the tip electrode protrudes through the distal opening, and an extended configuration in which the entire end section protrudes from the distal opening and assumes an arcuate shape; and
   an energy generator, which is configured to apply electrical energy only to the tip electrode while the probe is in the retracted configuration and to apply the electrical energy to at least the proximal electrodes while the probe is in the extended configuration, wherein the probe comprises a transducer, which is configured to provide a signal indicating that the probe is in the retracted configuration.

2. The apparatus according to claim 1, wherein the transducer is one of multiple position transducers, which are disposed along the end section and are configured to provide signals indication of a position of the end section within the body.

3. The apparatus according to claim 1, wherein the sheath comprises a positioning element in proximity to the distal opening, and wherein the energy generator is configured to apply the electrical energy only to the tip electrode when the signal provided by the transducer indicates that the transducer is within a predetermined minimum distance of the positioning element.

4. A method for treatment, comprising:
   inserting a sheath, having a lumen with a distal opening, into body of a patient;
   inserting a flexible probe through the sheath so that an end section, at a distal end of the probe, protrudes from the distal opening and assumes an arcuate shape;
   while the end section protrudes from the distal opening, bringing the arcuate shape into contact with tissue in the body and actuating a plurality of electrodes, distributed along the end section, to apply electrical energy to the tissue;

withdrawing the flexible probe into the sheath so that the end section is contained within the lumen and only a tip electrode, at a distal tip of the end section, protrudes through the distal opening; and while the end section is contained within the lumen, bringing the tip electrode into contact with the tissue, and actuating only the tip electrode with the electrical energy, wherein withdrawing the flexible probe comprises receiving a signal from a transducer in the probe indicating that the probe is in the refracted configuration.

5. The method according to claim 4, wherein receiving the signal comprises receiving signals from multiple position transducers, which are disposed along the end section and are configured to provide an indication of a position of the end section within the body.

6. The method according to claim 4, wherein the sheath comprises a positioning element in proximity to the distal opening, and wherein actuating only the tip electrode comprises applying the electrical energy only to the tip electrode when the signal provided by the transducer indicates that the transducer is within a predetermined minimum distance of the positioning element.

* * * * *